United States Patent
Iseberg et al.

(10) Patent No.: US 7,269,262 B2
(45) Date of Patent: *Sep. 11, 2007

(54) HEARING TEST APPARATUS AND METHOD HAVING AUTOMATIC STARTING FUNCTIONALITY

(75) Inventors: Steven J. Iseberg, Rolling Meadows, IL (US); Gregory R. Shaw, Calgary Alberta (CA); Erik C. Gundersen, Carol Stream, IL (US); Laurel Christensen, Arlington Heights, IL (US); Mead C. Killion, Elk Grove Village, IL (US)

(73) Assignee: Etymotic Research, Inc., Elk Grove Village, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/436,925

(22) Filed: May 18, 2006

(65) Prior Publication Data
US 2006/0204014 A1 Sep. 14, 2006

Related U.S. Application Data

(63) Continuation of application No. 09/517,042, filed on Mar. 2, 2000, now Pat. No. 7,050,592.

(51) Int. Cl.
*H04R 29/00* (2006.01)

(52) U.S. Cl. .................................. 381/60; 600/559
(58) Field of Classification Search .............. 381/60, 381/56, 58, 26, 312, 322, 328; 600/559; 607/57, 136, 139, 130; 73/585
See application file for complete search history.

(56) References Cited

U.S. PATENT DOCUMENTS 6,167,138 A * 12/2000 Shennib ....................... 381/60
6,231,521 B1 * 5/2001 Zoth et al. .................. 600/559
7,050,592 B1 * 5/2006 Iseberg et al. ................ 381/60

* cited by examiner

*Primary Examiner*—Vivian Chin
*Assistant Examiner*—Lun-See Lao
(74) *Attorney, Agent, or Firm*—McAndrews, Held & Malloy, Ltd.

(57) ABSTRACT

A hearing test device and method are disclosed which involve the placement of a testing probe in the ear canal of a test subject. The device analyzes responses to stimuli applied to the ear canal to determine whether the testing probe has been properly placed in the ear canal. The device may determine, for example, whether the probe is stable, whether it is sealed in the ear canal, whether the resulting volume of the ear canal is acceptable, and/or whether the stimuli delivery system is blocked in any way. If the device determines that the testing probe has been properly placed in the ear canal, the device automatically starts a hearing test without requiring any operator input.

31 Claims, 5 Drawing Sheets

HEARING TEST APPARATUS AND METHOD HAVING AUTOMATIC STARTING FUNCTIONALITY

RELATED APPLICATIONS

The present application is a continuation of U.S. patent application Ser. No. 09/517,042 titled "HEARING TEST APPARATUS AND METHOD HAVING AUTOMATIC STARTING FUNCTIONALITY" filed Mar. 2, 2000 now U.S. Pat. No. 7,050,592, the complete subject matter of which is hereby incorporated herein by reference, in its entirety.

FEDERALLY SPONSORED RESEARCH OR DEVELOPMENT

Not Applicable

MICROFICHE/COPYRIGHT REFERENCE

Not Applicable

BACKGROUND OF THE INVENTION

Hearing test devices that monitor the condition within a human ear are known. Such test devices generally require that the person performing the test (the "operator") place a test probe of the device within the ear canal of a test subject. Once the probe is placed properly within the ear canal, the operator activates the device, usually by pressing a button or the like. The device then emits test signals into the subject's ear through the probe in the ear canal. In response to the test signals emitted, the device receives response signals from the ear, likewise through the probe in the ear canal. Such response signals received are then used to determine whether the ear is functioning properly.

One such test device analyzes the distortion product otoacoustic emissions (DPOAE) generated by the ear to determine middle ear function. More specifically, a DPOAE test device generates and emits two audible tones (i.e., test signals) at different frequencies into the ear canal of a subject. A healthy ear will produce, in response to the two audible tones, a response signal having a frequency that is a combination of the frequencies of the two audible tones. Thus if the two audible tones generated have frequencies of f1 and f2, respectively, a healthy subject's ear will emit a response signal having a frequency that is a combination of f1 and f2. The strongest response signal occurs at a frequency of (2)(f1)-f2, and is referred to as the distortion product.

In addition, DPOAE test devices also generally modify the frequencies of the audible tones transmitted into the ear canal over time during the course of the test. In response, a healthy subject's ear will emit a distortion product having a frequency that similarly changes over time during the course of the test. Generally speaking, the lack of distortion product otoacoustic emissions from the ear during the course of the test is an indication of possible hearing loss.

Existing DPOAE test devices all use a probe that is inserted into the ear canal of the test subject. Such a probe is either attached to the device via a cable, or is mounted on the device to form an integrated hand-held device. In either case, proper placement of the probe into the ear canal is critical to obtaining accurate and useful DPOAE measurements. This is primarily due to the fact that otoacoustic emissions produced by a healthy ear are extremely small in magnitude, typically in the range from −10 dB SPL to +20 dB SPL. Improper placement of the test probe in the ear canal may result in the inadvertent masking of the emissions (and thus the triggering of a false negative response), in an inaccurate measurement, or in an otherwise invalid result. Proper placement of the test probe in the ear canal is generally determined by one or more of several factors. An operator may be required to insert the probe deeply into the ear canal and/or to create a seal between the probe and the ear canal. An operator may also be required to ensure that the probe is not blocked by a collapsed ear canal, by the canal wall itself, or by earwax. In addition, the operator may also be required to determine that, once the probe is inserted, the resulting volume of the ear canal is within a certain desirable range.

Consequently, it is often very difficult for an operator to know whether proper placement of the probe has been achieved before the operator initiates the testing process. Moreover, particularly in the case of an integrated hand-held device, the act of initiating the test (e.g., pressing a start button) may shift the placement of the probe in the ear canal, which in and of itself may cause an inaccurate measurement. As a result, an operator may be required to perform several tests in order to obtain accurate measurements, greatly slowing down the testing process.

In addition, in some cases, these problems may prevent an accurate measurement altogether. Specifically, a large proportion of DPOAE testing is performed on infants. Typically, the infant is asleep when the testing is performed so that movement (and thus noise) is minimal. The process of properly placing and positioning the probe into an infant's very small ear canal for the amount of time and number of iterations needed to obtain accurate results often wakes the infant, which often makes the test impossible to complete, particularly if the infant is crying.

Therefore, it is an object of the present invention to provide a test operator with an indication that the testing probe is properly placed within the test subject's ear canal.

It is also an object of the present invention to provide automatic initiation or starting of the test once the probe has been properly placed within the test subject's ear canal.

BRIEF SUMMARY OF THE INVENTION

A system, device and/or method that determines existence of at least one pre-test condition prior to testing hearing of a test subject, substantially as shown in and/or described in connection with at least one of the figures, as set forth more completely in the claims.

These and other advantages and novel features of the present invention, as well as details of an illustrated embodiment thereof, will be more fully understood from the following description and drawings.

DETAILED DESCRIPTION OF THE INVENTION

Figure 1:
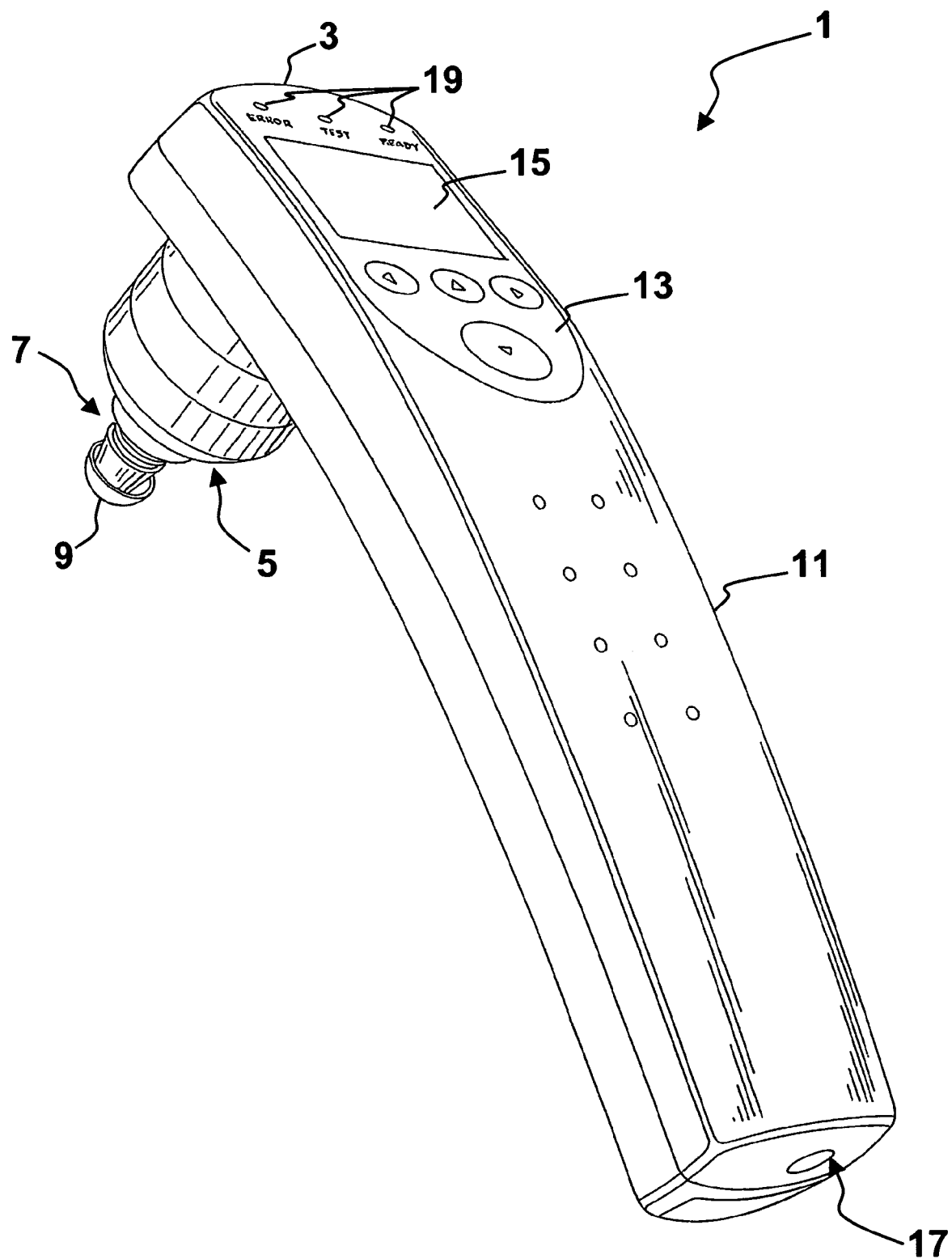
FIG. 1 illustrates an integrated, hand-held hearing test or screener device built in accordance with the present invention.

FIG. 1 illustrates an integrated, hand-held hearing test or screener device built in accordance with the present invention. The device 1 includes a housing or terminal portion 3, an isolation body or assembly 5 and a testing probe 7. The testing probe 7 includes an ear tip 9, which may be made of an elastic material, such as, for example, rubber. The testing probe 7 is integrated with the terminal portion 3 via the isolation body 5, which elastically couples or suspends the testing probe from the terminal portion 3. Additional detail regarding the isolation body 5 can be found in co-pending U.S. patent application Ser. No. 09/285,938 filed Apr. 2, 1999, now U.S. Pat. No. 6,299,584, issued Oct. 9, 2001, which is hereby incorporated herein by reference, in its entirety. While the testing probe 7 is illustrated in FIG. 1 as being integrated with the terminal portion 3, the testing probe 7 may be separate from the terminal portion 3 and connected to the terminal portion 3 via a cable (not shown). In addition, the device 1 itself may also be a stationary (i.e., not hand-held) device having a probe connected thereto via a cable, as is known in the art.

Referring again to FIG. 1, the terminal portion 3 includes a handle portion 11, a keyboard 13 and a display 15, which may be, for example, an LCD display. An operator grasps the handle portion 11, and manipulates the keyboard 13 with the operator's thumb (or forefinger). The operator may view the display 15 before, during and after the test. The terminal portion 3 also includes a data port (not shown) located on an underside of the handle portion 11. The data port enables the device 1 to be communicatively coupled to an external device, such as, for example, a personal computer, for download of test and related data or upload of programming or other information. The terminal portion 3 may also include additional visual indicators 19 (besides the display 15), such as, for example, light emitting diodes (LEDS), for indicating to the operator, for example, test status or the like. In FIG. 1, visual indicators 19 illustrate a "ready" status, a "test" status, and an "error" condition.

To perform a test, an operator grasps the handle portion 11 of the terminal portion 3 and moves the device 1 towards a test subject's ear (not shown). The operator then places the testing probe 7 into the subject's ear such that the ear tip 9 is seated within the subject's ear canal.

As explained more completely below, a pre-test condition analysis is initiated that determines whether certain condition(s) are satisfied, indicating that the testing probe is properly placed in the ear. Such analysis may be initiated automatically when the device is activated, or, automatically or by the operator when the testing probe 7 is placed in the subject's ear. In any case, if all condition(s) are satisfied, the actual ear test is automatically started by the device 1, without requiring operator input.

Figure 2:
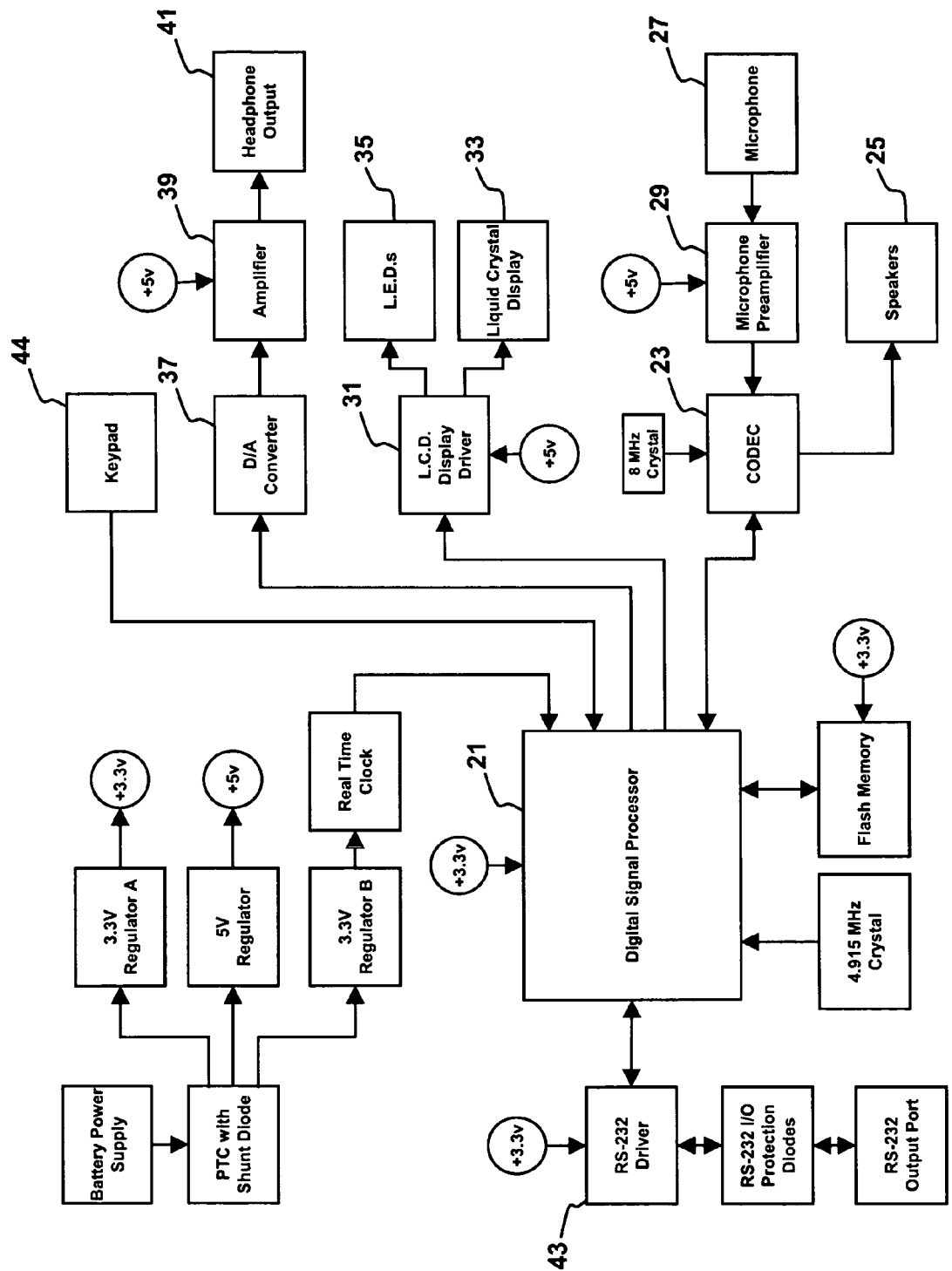
FIG. 2 is a block diagram of a hearing test or screener device built in accordance with the present invention.

FIG. 2 is a block diagram of a hearing test or screener device built in accordance with the present invention. The block diagram of FIG. 2 is one embodiment of the device 1 of FIG. 1, which may be used, for example, to perform DPOAE testing, as discussed above. Of course, other embodiments exist that may not incorporate all of the components shown in FIG. 2, or that may incorporate components that are different than, or components in addition to, those shown in FIG. 2.

The embodiment of FIG. 2 will now be discussed with reference to DPOAE testing. A digital signal processor (DSP) 21 generates digital signals representative of two audio tones of different frequencies and transmits the digital signals to a CODEC block 23 (i.e., an analog to digital and digital to analog converter), which converts the digital signals to electrical signals. The electrical signals are transmitted to an audio source 25, which may be, for example, located in the testing probe 7 of FIG. 1. The audio source 25 may comprise, for example, two audio speakers. The two audio speakers respectively transduce electrical signals into audible tones that are transmitted into the ear canal of a test subject. A microphone 27, which may, for example, be located in the testing probe 7 of FIG. 1, receives responsive audio signals from the ear of the test subject, and transduces the received audio signals into electrical signals representative of the received audio signals. The electrical signals are amplified by a microphone preamplifier 29, converted into digital signals by the block 23, and then communicated to the DSP 21. The DSP 21 then uses the signals to perform DPOAE analysis as is known in the art.

The DSP 21 also communicates output signals to the LCD Display Driver 31 which causes display of output data on the liquid crystal display 33 and/or indication of test status on visual indicators (e.g., LEDs) 35. In general, the output data comprises, for example, test results or the like. Output data, as such, may be displayed before, during and after the test. In fact, as discussed more completely below, the display may be used by an operator before the test to assist in properly placing the testing probe into the ear canal.

An operator may also use a headphone to further assist with proper placement of the testing probe in the ear. In one embodiment, the DSP 21 communicates digital signals (e.g., representative of the audio signals received from the ear) to a D/A converter 37, which converts the digital signals into electrical signals. The electrical signals are then amplified by the amplifier 39 and communicated to a headphone output 41. The headphone output 41, which may be, for example, headphone jack 17 shown in FIG. 1, is connected to a headphone assembly (not shown), which transduces the electrical signals into audio signals. Alternatively, the headphone output may be located adjacent the data port on the underside to the handle portion 11. With such a configuration, an operator may, for example, monitor the audio signals received from the ear to assist in the positioning and repositioning of the probe within the ear canal. Additional detail regarding audibly monitoring the condition in the ear can be found in co-pending U.S. patent application Ser. No. 08/971,520 filed Nov. 17, 1997, now U.S. Pat. No. 6,056,698 issued May 2, 2000, which application is hereby incorporated herein by reference, in its entirety.

In a further embodiment, discussed more completely below, the DSP 21 communicates status signals, to the headphone output 41, which signals can be audibly monitored by an operator via the headphones, to assist with the positioning of the probe within the ear canal.

The DSP 21 also downloads or uploads data via the data port by communication with the RS-232 driver 43. In addition, keypad 44 enables an operator to enter data and/or commands into the device 1.

As mentioned above, the actual testing phase performed by the testing device is automatically started after the testing probe has been placed in the ear canal and upon the completion of a pre-test condition analysis. In other words, the device does not begin the actual test until it determines that the testing probe has been properly placed in the ear canal.

Such auto-start functionality simplifies the testing procedure. Since the actual hearing test begins once it is determined that the probe is properly placed in the ear canal and without requiring further action by the operator, there is a greater chance that accurate data will be generated by the first hearing test attempt. As mentioned above, this is particularly important for infants, who are most often tested while they are sleeping. In addition, such auto-start functionality eliminates the potential movement problems associated with the operator pressing a button to initiate a test while the probe is in the subject's ear. This is particularly true for a hand-held device such as that shown in FIG. 1, since the action of depressing a key often results in inadvertent probe movement.

Figure 3:
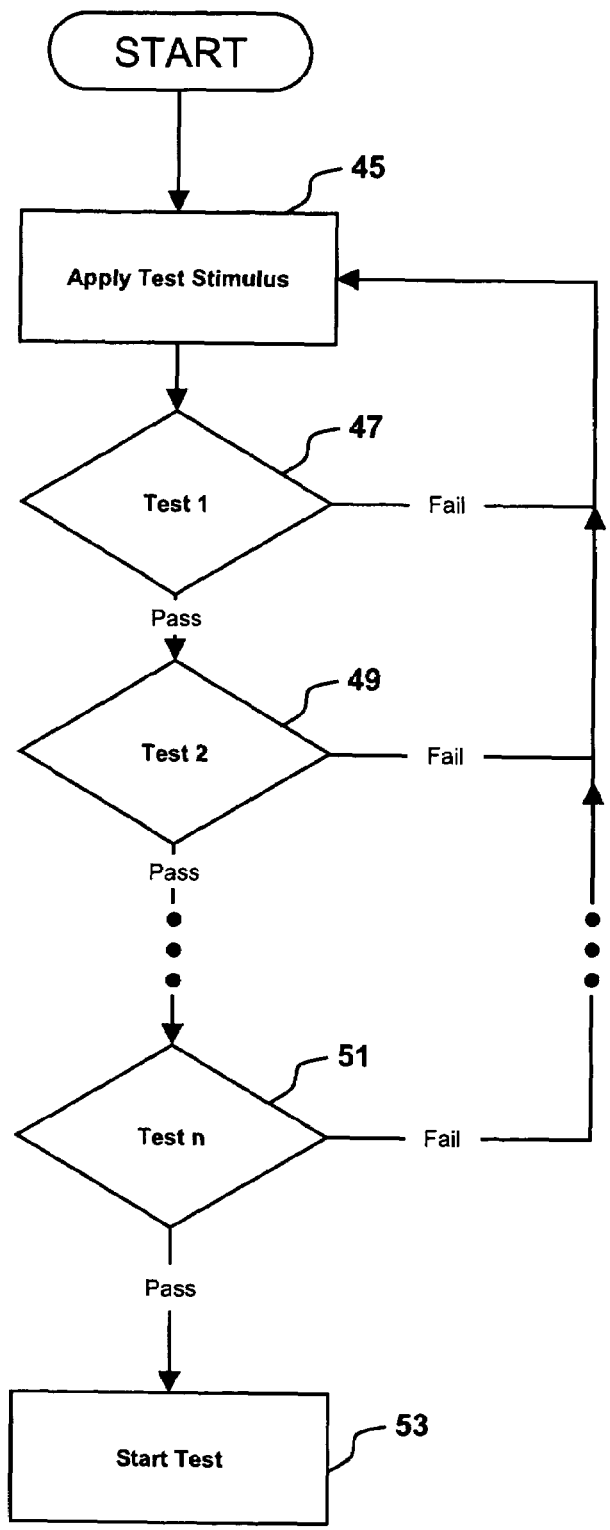
FIG. 3 is a flow chart illustrating generically the auto-start feature of the present invention.

FIG. 3 is a flow chart illustrating generically the auto-start feature of the present invention. The functionality of FIG. 3 may be implemented using a digital signal processor. As mentioned above, the auto-start feature of the present invention involves a pre-hearing test condition analysis. The analysis begins by application of a series of stimuli to the subject's ear (block 45) by a source, such as, for example, a speaker. A receiver, such as, for example, a microphone receives responsive signals from the ear, which are measured both over time and frequency. The measured signals are then used to perform one or more tests (blocks 47, 49, 51) to determine whether certain condition(s) exist (or do not exist, as the case may be) that indicate proper placement of the probe within the ear canal. If any one of the tests are failed (or if the single test is failed if only one test is being performed), the process begins over again by application of the stimuli at block 45. If, however, all of the tests are passed (or if the single test is passed if only one test is being performed), indicating that the proper condition(s) are present, the actual hearing test (e.g., a DPOAE test) is automatically initiated (block 53).

Figure 4:
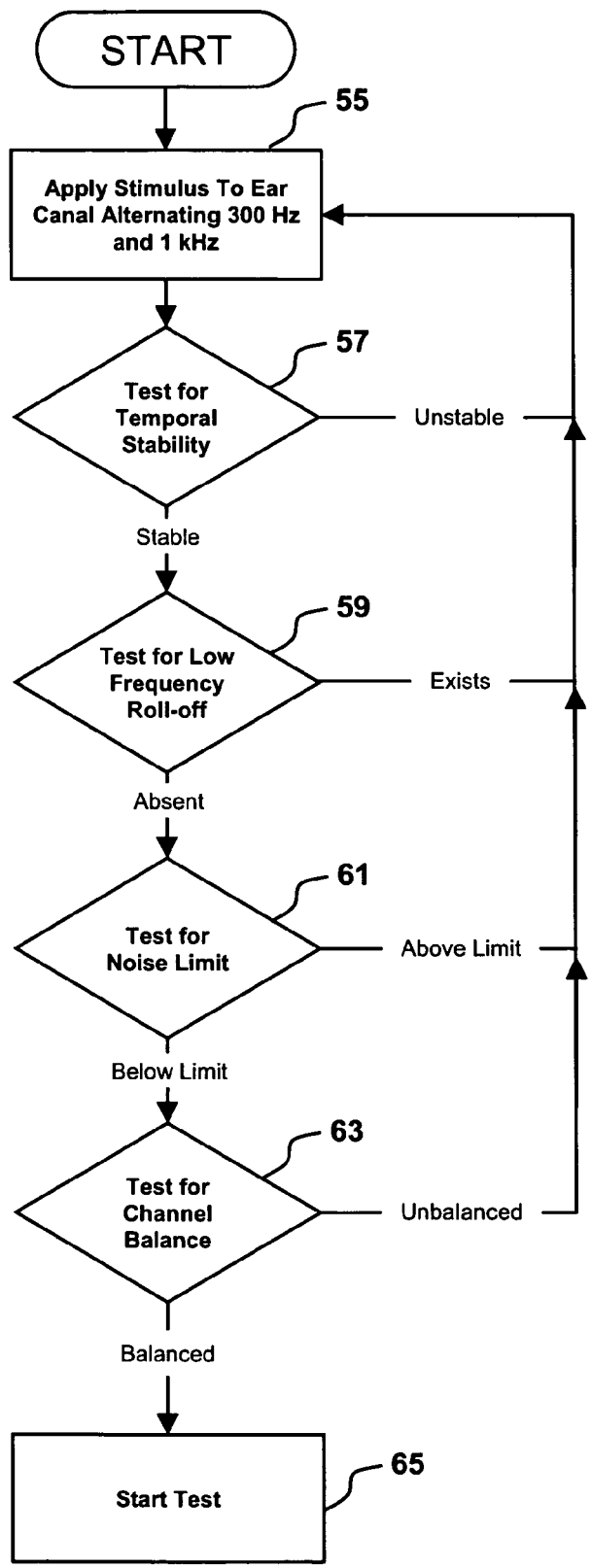
FIG. 4 is a flow chart illustrating the auto-start feature of the present invention, in which tests are performed to analyze four pre-start conditions, namely, temporal stability, low frequency roll-off, noise limit, and channel balance.

FIG. 4 is a flow chart illustrating the auto-start feature of the present invention, in which tests are performed to analyze four pre-start conditions, namely, temporal stability, low frequency roll-off, noise limit, and channel balance. The functionality of FIG. 4 may be implemented by the hearing test or screener device of FIGS. 1 and 2.

The analysis begins by the application of stimuli to the ear canal (block 55) via the source or speakers 25 of FIG. 2. As discussed above, the stimuli is generated by the DSP 21 of FIG. 2. Such stimuli may, for example, be alternating 300 Hz and 1 KHz audio tones. Such stimuli may also be non-audio stimuli. The microphone 27 receives responsive signals from the ear which are measured over time by the DSP 21 and used to perform condition tests.

The first test performed is determining the temporal stability condition (block 57). The general purpose of this test is to estimate when the position of the probe is stationary in the ear canal. Probe movement changes the geometry of the enclosed space in the ear behind the end of the probe tip, and thus changes the magnitude of the response received from the ear. When the magnitude of such response is consistent over time, temporal stability is assumed (i.e., the temporal stability condition is satisfied).

Referring to block 57 of FIG. 4, if it is determined that the probe is unstable, the temporal stability condition test begins over again at block 55. If, however, it is determined that the probe is stable, the next test is initiated. Additional detail regarding determining the temporal stability condition is set forth below.

The next test performed is determining the low frequency roll-off condition, i.e., whether the response received from the ear exhibits any low frequency roll-off (block 59). The low frequency roll-off condition may also be referred to as the spectral response condition. The general purpose of this test is to determine when the probe has formed a proper seal in the ear canal. When a probe is not completely sealed to the ear canal, the low frequencies (usually <500 Hz) show a pronounced decrease in magnitude. The lowest frequencies show the greatest decrease in magnitude, gradually decreasing as frequency increases. This condition is known as low-frequency roll-off. When the shape of the low frequency component of the response is determined to be within an acceptable range, the condition is satisfied. In making such a determination, both the slope of the low frequency component of the response and the range of values received may be considered.

Referring to block 59 of FIG. 4, if it is determined that the response exhibits low frequency roll-off, the process begins over again at block 55. If, however, it is determined that low-frequency roll-off is sufficiently absent from the response, the next test is initiated. Additional detail regarding determining the spectral response condition is set forth below.

The next test performed is determining whether any background noise is received along with the response from the ear (block 61). The general purpose of this test is to delay the starting of the hearing test if there is significant background noise present. A noise floor of the response may be determined from a frequency band where there is no stimuli energy. In one embodiment, the noise floor is calculated at the lowest frequency to be tested. When the noise floor is below an acceptable level, the test is passed. In general, if the noise level is too high, for example, if there is background noise in the test room or if the test subject is swallowing or coughing, the actual hearing test is delayed. Otherwise, the unwanted noise may mask the signals needed to perform the actual hearing test.

Referring to block 61 of FIG. 4, if it is determined that the noise floor is above the limit, the process begins over again at block 55. If, however, it is determined that the noise floor is below the limit, the next test is initiated.

The next test performed is determining the channel balance condition, i.e., whether any blockages exist in the sound delivery system (block 63). A set of stimuli is applied in an alternating fashion by the sound source (e.g., two speakers), and the response received from the ear canal is measured. If one of the responses is not received, then it is assumed that a blockage exists. In general, this test is passed when the responses received as a result of each speaker are within an acceptable range.

Referring to block 63 of FIG. 4, if the responses are not within an acceptable range, it is assumed that the channels are unbalanced and the process begins over again at block 55. If, however, the responses are within an acceptable range, it is assumed that the channels are balanced and the actual hearing test is started (block 65).

Thus, as can be seen in FIG. 4, the actual hearing test automatically starts if and only if all of the pre-hearing test or pre-start conditions are satisfied. A system such as in FIG. 4 may, however, incorporate an override feature that enables the actual hearing test to be started without performance of one or more of the condition tests. Such an override feature may be used in situations where a test subject's physiology prevents passage of one or more of the condition tests.. For example, if a test subject has a pressure equalization tube in the subject's tympanic membrane, the apparent ear canal volume would be abnormally large, preventing the actual hearing test from starting (e.g., the spectral response condition test would be failed). In one embodiment, the override feature is implemented so that a particular condition test (or tests) is disabled and thus skipped. In another embodiment, all condition tests are disabled, in which case the actual hearing test is manually initiated by the operator.

In addition, as can be seen from FIGS. 3 and 4, the overall testing process involves two phases, the auto-start phase, during which the condition tests are performed, and the hearing test phase, during which an actual hearing test (such as a DPOAE test discussed above) is performed. To assist an operator in positioning the probe in the ear canal during the auto-start phase, feedback may be provided to the operator. Such feedback informs the operator of the status of the auto-start phase, and may take the form of visual queues, auditory queues, or both. Examples of visual queues include light indicators (such as visual indicators 19 of FIG. 1), text messages provided on a display (such as display 15 of FIG. 1), and graphical outputs provided on such a display. Examples of auditory queues include audible tones, generated speech queues, and the actual response measured by the microphone (such as the microphone 27 of FIG. 2). Such auditory queues may be presented to the operator via external headphones, as discussed above with respect to FIG. 2, and may comprise distinctive sounds for each condition test performed during the auto-start phase.

While FIG. 4 shows four condition tests being performed, it should be understood that any number of those tests can be implemented in any given system. For example, following this description and prior to the claims is 6 pages of an exemplary computer code listing (hereinafter referred to as "the Code") in which only the condition tests of blocks 57, 59 and 63 of FIG. 4, namely, the temporal stability condition test, spectral response condition test, and receiver balance condition test, are performed. The Code is one embodiment of the auto-start phase that may be used by the device of FIGS. 1 and 2, and is being submitted as part of the specification pursuant to 37 C.F.R. §1.96(b)(2).

The auto-start phase as set forth in the Code may be described as follows. The stimuli applied to the ear canal consists of two pure tones at different frequencies (F1, F2), with one tone applied per speaker. The tones F1 and F2 may be 300 Hz and 1000 Hz, for example. The response is measured over a fixed interval of time. The frequency of the tones are then reversed on the speakers and the response is measured again. This complete sequence is completed at least once, resulting in each speaker sending out four tones. Specifically, this complete sequence may be illustrated as follows:

| Stimuli # | Speaker A | Speaker B |
|---|---|---|
| n − 3 | F1 | F2 |
| n − 2 | F2 | F1 |
| n − 1 | F1 | F2 |
| n | F2 | F1 | where n is the most recent stimuli. The stimuli may be applied every one-third of a second, for example, resulting in a complete sequence time of 1.2 seconds.

The complete sequence, therefore, starts with the initiation of the first stimuli (n-3), where Speaker A transmits a tone at F1 (e.g., 300 Hz) and speaker B transmits a tone at F2 (e.g., 1000 Hz). One third of a second later, the second stimuli (n-2) is initiated, where speaker A transmits a tone at F2 (1000 Hz) and speaker B transmits a tone at F1 (300 Hz). One third of a second later, the third stimuli (n-1) is initiated, where speaker A again transmits a tone at F1 and speaker B transmits a tone at F2. Finally, after another one third of a second, the fourth stimuli (n) is initiated, where again speaker A transmits a tone at F2 and speaker B transmits a tone at F1.

Next, the responses to each tone transmitted are measured, where Pi(n) is the measured pressure (in dB) at frequency F1 for each stimuli n. The pressure values (i.e., responses) are then used to perform the condition analysis.

More particularly, with regard to the temporal stability condition, the responses from each speaker are compared over time at each frequency according to the following equations:

Speaker A $|P1(n-1)-P1(n-3)| <= \text{fit\_bal2}$ (F1)

$|P2(n)-P2(n-2)| <= \text{fit\_bal2}$ (F2)

Speaker B $|P1(n)-P1(n-2)| <= \text{fit\_bal2}$ (F1)

$|P2(n-1)-P2(n-3)| <= \text{fit\_bal2}$ (F2)

where fit_bal2 is the temporal balance parameter (in dB). The value of the temporal balance parameter, which may be, for example 2 dB, establishes how closely the response at each frequency must match in order to conclude that the probe is stable.

Specifically, for speaker A, the difference between the responses for the first tone (F1) (i.e., the difference in pressure resulting from the first and third stimuli) is calculated. Also, the difference between the responses for the second tone (F2) (i.e., the difference in pressure resulting from the second and fourth stimuli) is calculated. The same two calculations are also performed for speaker B. If all four calculated values are no greater than 2 dB, for example, then the temporal stability test is passed, and the conditional analysis proceeds to the spectral response condition test.

The spectral response condition test determines the difference in the response as a function of frequency, according the following equations:

$|P2(n)-P1(n-1)| <= \text{fit\_bal3}$ Speaker A $|P1(n)-P2(n-1)| <= \text{fit\_bal3}$ Speaker B where fit_bal3 is the spectral response parameter (in dB). In other words, the response generated by each speaker is compared at different frequencies (e.g., 300 Hz v. 1000 Hz) to determine if a leak in the probe seal exists. If the calculated difference between the response generated by each speaker is no greater than say, for example, 25 dB, then it is assumed that no leak is present.

The spectral response condition test also determines the average receiver response to the first tone (F1) according to the following equation:

$$\text{Speaker} \quad B \quad A$$
$$\text{fit\_min} \pounds |(P1(n)+P1(n-1))/2| <= \text{fit\_max}$$

where fit_min is the minimum spectral response at F1 (in dB) and fit_max is the maximum spectral response at F1 (in dB). This calculation is essentially a test of the volume of the ear canal. If the average response is within an acceptable range (e.g., between 32 dB and 50.5 dB), then the volume is of the size expected from an ear canal. If the average response is greater than the range, the volume is too small, indicating a blocked or partially blocked condition. If the average response is below the range, the volume is too large, indicating that the probe is not in the ear canal (or not far enough in).

When the "leak" and "volume" portions of the spectral response condition test are passed, it is assumed that the probe is placed a proper distance in the ear canal and the probe is properly sealed to the canal. The condition analysis then proceeds to the channel balance condition test.

The channel balance condition test compares the response generated by each speaker at the same frequency according to the following equation:

Speakers $B$ $A$ (F1)
$$|P1(n) - P1(n-1)| <= \text{fit\_bal1}$$

Speakers $A$ $B$ (F2)
$$|P2(n) - P2(n-1)| \pounds \text{fit\_bal1}$$

where fit_bal is the receiver balance parameter (in dB). In other words, the response generated by tone F1 is compared at each speaker, and the response generated by tone F2 is compared at each speaker. If both comparisons result in a value of no greater than 4 dB, for example, then it is assumed that both speakers are functioning (e.g., neither is blocked). Once this test is passed, the actual hearing test is automatically started.

Again, in the present embodiment, all condition tests must be passed for the actual hearing test to be automatically started. If any fail, the process begins over again by the transmission of two more sets of tones are transmitted (corresponding to fifth and sixth stimuli). The responses are then reevaluated. Specifically, fifth and sixth sets of responses are generated, and they are used with the third and fourth sets of responses in performing the condition tests over again. The first and second sets of responses are discarded. If one of the condition tests is again failed, two more sets of tones are transmitted (corresponding to seventh and eighth stimuli), and seventh and eighth sets of responses are generated. They are used with the fifth and sixth sets of responses in performing the condition tests over again. The third and fourth sets responses are discarded. This process is repeated until all condition tests are passed.

Figure 5:
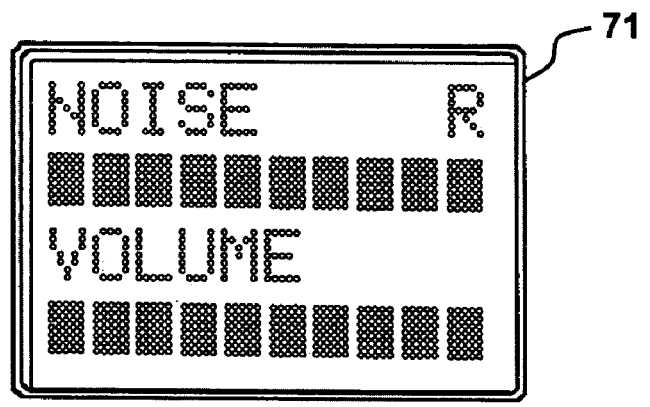
FIG. 5 depicts screens that illustrate, via bar graph, volume and noise levels measured by the device.
Figure 5:
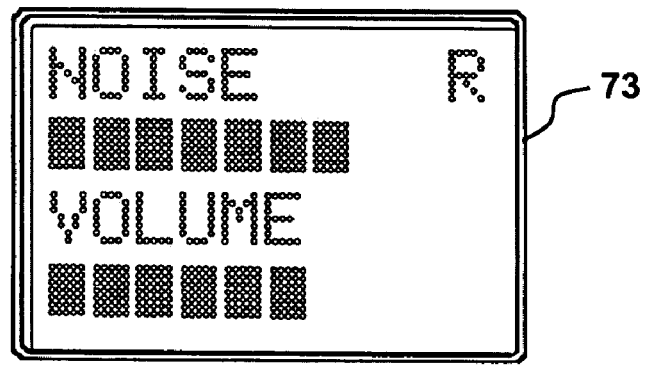
Figure 5:
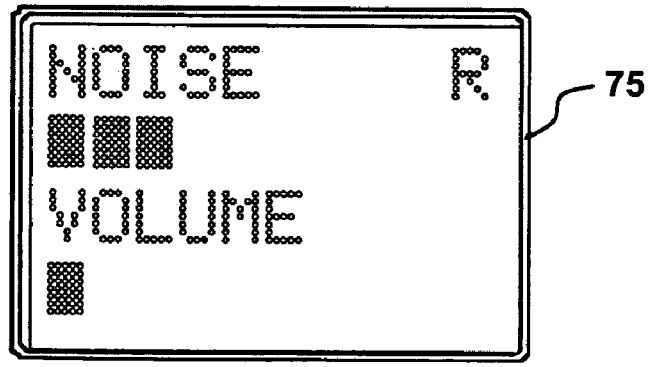

As mentioned above, it may be desirable to provide the operator feedback during the auto-start phase of the testing process. The Code provides for display of data to assist the operator in positioning the probe in the ear canal. FIG. 5 depicts screens that illustrate, via bar graph, volume and noise levels measured by the device. Screen 71 shows a condition where the noise and volume are high, indicating that the probe has not yet been placed in the ear canal. Screen 73 shows a condition where the noise and volume are lower, indicating to the operator that, while the probe is being positioned in the ear canal, it has not been inserted properly (e.g., the probe is not deep enough and not sealed to the ear canal). Screen 75 shows a condition where the noise and volume are relatively low, indicating to the operator that the positioning is likely proper, and that the actual hearing test may be started soon. Of course, other types of outputs on the display are also possible, as mentioned above, to assist the operator.

These and other objects of the invention are achieved in a hearing test device that transmits pre-hearing test condition analysis stimuli into the ear canal of a test subject. The device analyzes signals received from the ear canal in response to the stimuli, and determines from the stimuli a condition or conditions related to the position of the testing probe in the ear canal. If the condition or conditions are satisfied, the device automatically begins a hearing test. Satisfaction of the condition or conditions as such generally indicates that the testing probe is placed properly in the ear canal.

In one embodiment, the condition comprises a temporal stability condition, which is a measure of the stability of the testing probe in the ear canal. If it is determined that the testing probe is stable (i.e., stationary for a period of time) in the ear canal, the temporal stability condition is satisfied.

In another embodiment, the condition comprises a spectral response condition, which is a measure of the seal of the testing probe and of the volume of the ear canal. If it is determined that the testing probe is sealed in the ear canal and the volume of the ear canal is within an acceptable range, the spectral response condition is satisfied.

In yet another embodiment, the condition comprises a channel balance condition, which is a determination of whether any blockages exist in the sound delivery system. If a response is not received to one of the stimuli, then a blockage is assumed. If the responses received are within an acceptable range, then the condition is satisfied.

The hearing test device also includes a display that provides an indication of the volume behind the testing probe, as well as the noise being received by the device, to assist the operator in properly positioning the testing probe in the test subject's ear canal.

Many modifications and variations of the present invention are possible in light of the above teachings. Thus, it is to be understood that, within the scope of the appended claims, the invention may be practiced otherwise than as described hereinabove.

What is claimed is:

1. A hearing test device comprising:
   signal generation circuitry for generating audio frequency signals for transmission, via a test probe, into an ear canal of a test subject;
   receiver circuitry for processing response signals received from the ear canal of the test subject;
   at least one processor for determining, using at least the response signals, that at least one pre-test condition of the test probe is satisfied; and
   user feedback circuitry, communicatively coupled to the at least one processor, to aid a user in proper probe placement.

2. The hearing test device of claim 1, wherein the audio frequency signals comprise one or more pure tones.

3. The hearing test device of claim 1, wherein the at least one pre-test condition is satisfied upon detection of temporal stability of the test probe.

4. The hearing test device of claim 3, wherein temporal stability is indicated when response signals have an essentially consistent magnitude over a period of time.

5. The hearing test device of claim 1, wherein the at least one pre-test condition is satisfied upon detection of proper placement of the test probe in relation to the ear canal.

6. The hearing device of claim 5, wherein proper placement is indicated when low frequency roll-off of the response signals is within a predetermined range.

7. The hearing test device of claim 1, wherein the at least one pre-test condition is satisfied upon detection of an acceptable level of noise in the response signals.

8. The hearing text device of claim 7, wherein an acceptable level is less than a predetermined noise level.

9. The hearing test device of claim 1, wherein the at least one pre-test condition is satisfied upon detection of proper functioning of the test probe in transmitting audio frequency signals and receiving response signals.

10. The hearing device of claim 9, wherein proper functioning is indicated when the amplitude of the response signals in the presence of generated audio frequency signals is above a predetermined level.

11. The hearing test device of claim 1, wherein the user feedback circuitry comprises a visual display.

12. The hearing test device of claim 11, wherein the visual display comprises a light emitting diode display.

13. The hearing test device of claim 1, wherein the feedback circuitry is located proximate the test probe.

14. The hearing test device of claim 1, wherein the user feedback circuitry comprises an audible signal.

15. The hearing test device of claim 1, wherein the determining automatically proceeds upon placement of the test probe in an ear of the test subject.

16. The hearing test device of claim 1, wherein the hearing test device further comprises:
data port circuitry for communication with a device external to the hearing test device.

17. The hearing test device of claim 1, wherein the processor automatically performs a hearing test on the test subject upon determining satisfaction of the at least one pre-test condition.

18. The hearing test device of claim 16, wherein the hearing test comprises a distortion product otoacoustic emissions (DPOAE) test.

19. The hearing test device of claim 1, wherein the test probe, during use, is positioned within the ear canal.

20. A method of operating a hearing test device, the method comprising:
receiving information identifying, from a plurality of pre-test conditions for determining whether a testing probe is properly positioned in an ear canal, pre-test conditions to be satisfied before initiation of a hearing test;
performing pre-testing to determine whether all identified pre-test conditions are satisfied;
automatically initiating the hearing test, if all identified pre-test conditions are satisfied; and
continuing performing pre-testing, if all identified pre-test conditions are not satisfied.

21. The method of claim 20, wherein the information identifying pre test conditions is received from a device external to the hearing test device.

22. The method of claim 20, wherein the information identifying pre test conditions is received via user input at the hearing test device.

23. The method of claim 20, wherein the plurality of pre-test conditions comprises one or more of a temporal stability condition, a spectral response condition, a channel balance condition, and a noise level condition.

24. The method of claim 23, wherein the temporal stability condition is satisfied when response signals received from an ear canal of a test subject in response to an audio signal transmitted into the ear canal are consistent in magnitude over a period of time.

25. The method of claim 23, wherein the spectral response condition is satisfied when the difference in magnitude of response signals received from an ear canal of a test subject in response to audio signals of different frequencies transmitted into the ear canal is less than a predetermined value.

26. The method of claim 23, wherein the channel balance condition is satisfied when each of two response signals received from an ear canal of a test subject in response to each of two audio signals transmitted into the ear canal using separate audio transducers differs by no more than a predetermined amount.

27. The method of claim 23, wherein the noise level condition is satisfied when a noise level of a response signal received from an ear canal of a test subject is no greater than a predetermined value.

28. The method of claim 20, further comprising:
downloading hearing test data to a device external to the hearing test device.

29. The method of claim 20, further comprising:
notifying a user when all identified pre-test conditions are satisfied.

30. The method of claim 29, wherein the notifying comprises a visual indication.

31. The method of claim 20, wherein the hearing test comprises a distortion product otoacoustic emissions (DPOAE) test.

* * * * *